US007365175B2

(12) United States Patent
Nishimura et al.

(10) Patent No.: US 7,365,175 B2
(45) Date of Patent: Apr. 29, 2008

(54) WIT 3.0, A NOVEL GENE TO CONTROL SOFT TISSUE WOUND HEALING

(75) Inventors: Ichiro Nishimura, Los Angles, CA (US); Cortino Sukotjo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 60 days.

(21) Appl. No.: 10/170,786

(22) Filed: Jun. 12, 2002

(65) Prior Publication Data
US 2003/0092030 A1    May 15, 2003

(51) Int. Cl.
C07H 21/02 (2006.01)
C07H 21/04 (2006.01)
A61K 38/00 (2006.01)

(52) U.S. Cl. .................. 536/23.1; 435/69.1; 435/325; 435/253.3; 514/44

(58) Field of Classification Search ............... 536/23.1; 435/320.1, 69.1, 325, 252.3, 253.3; 514/44
See application file for complete search history.

(56) References Cited

U.S. PATENT DOCUMENTS 5,670,367 A * 9/1997 Dorner et al. ........... 435/320.1
6,130,038 A * 10/2000 Becker et al. ................. 435/6

FOREIGN PATENT DOCUMENTS

JP              1074617       *  2/2001

OTHER PUBLICATIONS

Carninci, P. et al. (2000) Normalization and subtraction of cap-trapper-selected cDNAs to prepare full-length cDNA libraries for rapid discovery of new genes. Genome Res. vol. 10, pp. 1617-1630.*
Shibata, K. et al. (Nov. 2000) RIKEN integrated sequence analysis (RISA) system—384-format sequencing pipeline with 384 multicapillary sequencer. Genome Res. vol. 10, pp. 1757-1771.*
Carninci, P. et al. (1999) High-efficiency full-length cDNA cloning. Methods Enzymol. vol. 303, pp. 19-44.*
Darnell, J. et al. (1990) In "Molecular Cell Biology" (2nd edition) p. 86.*
Attachment 1: sequence alignment (pp. 1-2).*
Attachment 2: the sequence of Accession No. AK004662.*
Attachment 3: the sequence of Accession No. AK050102.*
Attachment 4: sequence alignment (pp. 1-2).*
Attachment 5: sequence alignment (pp. 1-2).*
Attachment 6: Scientific name : expression vector plasmid pME18S-FL3 (p. 1).*
Attachment 7: "Meaning of transformant", form hyperdictionary. p. 1.*
Guhaniyogi et al. (2001) Regulation of mRNA stability in mammalian cells. Gene. vol. 265, Nos. 1-2, pp. 11-23.*
Cowin et al. (2006) Wound Healing Is Defective in Mice Lacking Tetraspanin CD151. J. Invest. Dermatol. pp. 1-10. 9Epub ahead of print).*
Berditchevski et al. (2001) Analysis of the CD151-alpha3beta1 integrin and CD151-tetraspanin interactions by mutagenesis. J. Biol. Chem. vol. 276, No. 44, pp. 41165-41174.*
Tanaka et al. (2000) Genome-wide expression profiling of mid-gestation placenta and embryo using a 15,000 mouse developmental cDNA microarray. Proc. Natl. Acad. Sci. U S A., vol. 97, No. 16, pp. 9127-9132.*
Puoti et al. (1997) Novel isoforms of the beta and gamma subunits of the Xenopus epithelial Na channel provide information about the amiloride binding site and extracellular sodium sensing. Proc. Natl Acad. Sci. U S A. vol. 94, No. 11, pp. 5949-5954.*
Chakrabarti et al. (1985) Vaccinia virus expression vector: coexpression of beta-galactosidase provides visual screening of recombinant virus plaques. Mol. Cell. Biol. vol. 5, No. 12, pp. 3403-3409.*
Okayama et al. (1987) High-efficiency cloning of full-length cDNA; construction and screening of cDNA expression libraries for mammalian cells. Methods Enzymol. vol. 154, pp. 3-28.*
Kim et al. (2001) Antisense expression of an Arabidopsis ran binding protein renders transgenic roots hypersensitive to auxin and alters auxin-induced root growth and development by arresting mitotic progress. Plant Cell. vol. 13, No. 12, pp. 2619-2630.*
Helfman et al. (1987) Use of antibodies to screen cDNA expression libraries prepared in plasmid vectors. Methods Enzymol. vol. 152, pp. 451-457.*
Mylne et al. (1998) Binary vectors for sense and antisense expression of Arabidopsis ESTs. Plant Mol. Biol. Reporter, vol. 16, pp. 257-262.*
Frommm et al. (1985) Expression of genes transferred into monocot and dicot plant cells by electroporation. Proc. Natl. Acad. Sci. U S A. vol. 82, No. 17, pp. 5824-5828.*
Mouse Gene fgfr1op2 Description (2006) http://hgw7.cse.ucse.edu/cgi-bin/hgGene?org=Mouse&hgg gene=NM 026218&hgg chrom=none&db=mm8, p. 1.*
NCBI Sequence Revision History (2006) http://www.ncbi.nlm.nih.gov/entrez/sutils/girevhist.cgi?val=AK005320, p. 1.*
Jahangiri, L. et al., Current Perspectives in Residual Ridge Remodeling and its Clinical Implications: A review, Journal of Prosthetic Dentistry, (1998) vol. 80:224-237.
DelRio, M. et al., 1999, Nonviral Transfer of Genes to Pig Primary Keratinocytes Induction of Angiogenesis by Composite grafts of Modified Keratinocytes Overexpressing VEGF Driven by a Keratin Promoter, Gene Therapy, (1999) 6: 1734-1741.
Bryant, M. et al., Tissue Repair With a Therapeutic Transcription Factor, Human Gene Therapy , Oct. 10, 20002, 11: 2143-2158.
Sukotijo C. et al., Molecular Cloning of Wound Inducible Transcript (wit 3.0) Differentially Expressed in Edentulous Oral Mucosa Undergoing Tooth Extraction Wound-healing, Journal of Dental Research, Apr. 2002, vol. 81, No. 4, 229-235.

* cited by examiner

Primary Examiner—Nashaat T. Nashed
Assistant Examiner—Samuel Wei Liu
(74) Attorney, Agent, or Firm—Townsend and Townsend and Crew LLP

(57) ABSTRACT

The present invention provides a method of treatment to improve wound healing and to minimize/prevent abnormal scarring caused by tissue contraction and fibrosis formation by providing a specific gene, Wit 3.0 alpha and beta sequences that is differentially expressed in wounded oral mucosa cells, relative to their decreased expression in non-wounded oral mucosa cells. One aspect of the invention is a method to treat soft tissue wound using anti-sense nucleic acid technologies. Another aspect of the present invention is a method to treat soft tissue wound using sense nucleic acid technologies. These methods can employ a complimentary nucleic acid sequence that is greater than 85% identity to Wit 3.0 alpha and/or beta sequences or greater than 90% identity to the deduced amino acids thereof.

11 Claims, 10 Drawing Sheets

```
5' A CGC GGG GGA AGT CTC GCGAGG CTT GTC GCT GTG TGG CTG CCA GTA GCG GAG
GTT CTG GTC CGC CCG GGA TGG AGC CGA GGC AAG CGG GCT GCC GGA TCC TCC CTG
CCG CTG TGT GAG CAG CGC TGT GCG TCC GCT CGC TGA GCA GGC GCA GCG AGG CCG
CGG AGA GCA CTC TCT GGG CGC CTC CAT CTC GCG GGT GGT GGT CGC CGT CTC TGA
CGG CTG AGG GGG ACT GAA GCT GAG TGG AAA AAC ACG AGT GGG TGA ACC TCT GAG
CCG GGC TCC CTG TCT CCG TGC TCT CAC TGA GCT CCT GCC GGG AAC AGA GAA ATG
AGC TGC ACC ATT GAG AAG GCA CTT GCT GAT GCT AAG GCC CTT GTT GAA CGG TTG
AGA GAC CAT GAT GAT GCA GCA GAG TCT CTC ATC GAA CAG ACC ACT GCC CTC AGC
AAG CGA GTG GAA GCC ATG AAA CAG TAT CAG GAA GAA ATC CAA GAA CTT AAT GAA
GTA GCA AGA CAT CGG CCA CGA TCC ACA CTA GTT ATG GGA ATC CAG CAA GAA AAC
AGA CAA ATC AGA GAA TTC CAA CAA GAG AAC AAA GAA CTG CGC ACA TCC TTG GAA
GAG CAC CAG TCT GCC TTG GAA CTG ATA ATG AGC AAG TAT CGA GAG CAG ATG TTC
AGA TTG CTA ATG GCC AGC AAG AAG GAC GAC CCG GGC ATA ATA ATG AAG TTA AAG
GAG CAG CAC TCA AAG GAG TTG CAA GCA CAT GTT GAC CAG ATC ACC GAG ATG GCA
GCA GTA ATG AGA AAA GCT ATT GAA ATT GAC GAA CAG CAG GGT TGC AAG GAA CAG
CAG CGC ATA TTT CAA CTT GAA CAA GAA AAC AAA GGC TTG AGA GAG ATC CTT CAG
ATA ACT CGA GAA TCC TTT TTG AAC CTT CAG AAG GAT GAT GCG TCA GAG AGT ACA
TCT CTG TCC GCC TTA GTG ACT AAC AGT GAC CTG AGT CTG AGG AAG AGC TGA GTG
GTT GGC TGA GGT CAC TAA GAC GGG CCC AGG AGT GAG TGG ATG GAT GAA CAT AAA
CCC AAC TCC AGT CAG CCT CTT TCC TCT AGT ATG TCA GGG GCA CTG GCG AAG AGA
CAG TAG CAG GAT GTA TAG CCA GTG GTC ATA AAC TAG ATC CCA GTC ACA GCT CGA
CAG GAA AAC CTG GGC CAC AGA GTG AAC ATT GAG TCT CCA AGG TGC TGC TGA GGA
CTG CAA TTT GAG AAG TGC TGT TGG CCT CTT GGA TGA GAT ATG GGT CAC CCT GAA
TGC TCC TAA TAA ACG TCG GAA AGC CTA AAT TAT CAC AAC TCC AAA AGA AGG TTG
GTG TGG TGT TCT GGA TGG AAG ACT TTG TTC TGA TTC CTG TCC TTC TGT TCA GTG
TCA GAG TCA GCA TAG CTT ATG TAT GTA CCG CTT CTG TCT CGG TGC TCC CAT CCC
CCT GCC CAT CTG TTC ATC GCC GGC AGT TCA CAT TTA CAG GCT ATA GGA ATA TGT
CAC TCG CAT CAC AAA CTG AAG AAA GGA ATA TAC TTG CAC CTA GTT CCC ATA ACT
CTT AAC TAG CAA GTT ATT CGT GAC TTG CTT GAG TAT ATG TAC CTC AGG AAG GAA
GGA AAG ACA AGA ATA TAC TTT CTA AGA AAG ACA GTT TTA TAT AGA CAC ATT TAG
TAG GTT AAA CTA CTT TGA GAG ACT ATG TTT GGT TCT CTG TTA ACA ATG AGC CTG
GCT CTT CCT CCT CTC TAC ATG ATG TTT AAG GAT ACA GGA CAG AGG GGT TGG GGA
TTT AGC TCA GTG GTA GAG CGC TTG CCT AGC AAC CGC AAG GCC CTG GGT TCG GTC
CCC AGC TCC TAA AAA AAG GGA AAA AAA AAA GGA TAC AGG ATA GCT CAC TAG TAC
ACA GAG TTG GCA TAT TTA ATG TAA TAA GAT AGG TAT GGT CAT TTC CAA GTA AAT
TTG GAA TTC TTT GGT ATT TAA AAA AAC ACC TCT TCA AAC ATA TAA GTA AGA AAG
CAG GCT CCA AAA TCA AAG TTC TGG GAC TGA GTC TAA ACC CTG TTT AGT TCT TAT
AAC CTG TGA TTT TTC CCT ACA ACC TGT GAC TCA NAA ACT GGC AGT GAA AGT GTG
GGC CCA CAG GCA TTG TGC TTT GCA CTT AAA AAA AAA AGC TTA AGA CCA CAA
GAT AGA GAA GTG TGC TTT AAT ACC ATT GCA GCC TAA ACT CTT CTG TAG TGA TCA
GAA TAA AAG AAT AAA AGA TTG TGA AAT ACG GCA AAA AAT ATA CAA TAC TTG TAT
GTG AAG TTA GCA GAT AAA AGT AAA TCA TTT GTA AGT ACA TAT TAC TTT GCA
GTG TAA TTT TAT GTG TAA TTT CAT GTA TTG GCA AAA TTC ATA GGA CTT TTA CTT
GAG AAC CTT TCA TTC TGA AGT TTG AGG TGA GTG GGG TCA TAG GTC AGG TAG GAA
AGG GCC AGT ACC CCA GGT GAT AAA CCG TTG TCA TGC AGA GGC TTT AAT ATT TTA
TAT TTA GGT GAA TTT ATT TCT AAG ACT TTT CTA TTG GTT CTG GGA GAG TGT CCC
TTA GTT TAG TGG TCA TTC TTT CAT GTA GTT TGG CTC CAG GCC AGA ATC TTA GAA
GAA AGG CTA CAC AGT TGA GAT GAG GCA GAA TCA GGA GTG AGT AG TTC TAT TGT
GAA ATG TTA TTT CAG AAG TAA TTA TTT TTA TAA AAA AAT TAT TTA CTC TTT GTC
TTC TTG GAT ATA AGT TTA AGG TTG TGA ATA TTG AAA GAC ATT TGC ATT GTT CTT
AGC AAG TTT TCC ATC CCT CCT ATC ACC CCC CCC CTA AAA AAA AAA AAA 3'
```

SEQ ID NO: 1

FIGURE 1

```
  1  MSCTIEKALA  DAKALVERLR  DHDDAAESLI  EQTTALSKRV  EAMKQYQEEI
 51  QELNEVARHR  PRSTLVMGIQ  QENRQIREFQ  QENKELRTSL  EEHQSALELI
101  MSKYREQMFR  LLMASKKDDP  GIIMKLKEQH  SKELQAHVDQ  ITEMAAVMRK
151  AIEIDEQQGC  KEQQRIFQLE  QENKGLREIL  QITRESFLNL  QKDDASESTS
201  LSALVTNSDL  SLRKS
```

SEQ ID NO: 2

*Figure 2*

```
5'  ATG AGC TGC ACC ATT GAG AAG GCA CTT GCT GAT GCT AAG GCC CTT GTT GAA CGG
    TTG AGA GAC CAT GAT GAT GCA GCA GAG TCT CTC ATC GAA CAG ACC ACT GCC CTC AGC
    AAG CGA GTG GAA GCC ATG AAA CAG TAT CAG GAA GAA ATC CAA GAA CTT AAT GAA GTA
    GCA AGA CAT CGG CCA CGA TCC ACA CTA GTT ATG GGA ATC CAG CAA GAA AAC AGA CAA
    ATC AGA GAA TTC CAA CAA GAG AAC AAA GAA CTG CGC ACA TCC TTG GAA GAG CAC CAG
    TCT GCC TTG GAA CTG ATA ATG AGC AAG TAT CGA GAG CAG ATG TTC AGA TTG CTA ATG
    GCC AGC AAG AAG GAC GAC CCG GGC ATA ATA ATG AAG TTA AAG GAG CAG CAC TCA AAG
    ATT GAC ATG GTA CAT CGT AAC AGC TGC GAA GGA TTC TTC CTG GAT GCA TCT CGG CAC
    ATC CTT GAA GCA CCT CAG CAC GGA CTG GAG AGG AGG CAC TTG GAA GCA AAT CAG AAT
    GAG TTG CAA GCA CAT GTT GAC CAG ATC ACC GAG ATG GCA GCA GTA ATG AGA AAA GCT
    ATT GAA ATT GAC GAA CAG CAG GGT TGC AAG GAA CAG CAG CGC ATA TTT CAA CTT GAA
    CAA GAA AAC AAA GGC TTG AGA GAG ATC CTT CAG ATA ACT CGA GAA TCC TTT TTG AAC
    CTT CAG AAG GAT GAT GCG TCA GAG AGT ACA TCT CTG TCC GCC TTA GTG ACT AAC AGT
    GAC CTG AGT CTG AGG AAG AGC TGA 3'

SEQ ID NO: 3
```

Figure 3

```
  1  MSCTIEKALA  DAKALVERLR  DHDDAAESLI  EQTTALSKRV  EAMKQYQEEI
 51  QELNEVARHR  PRSTLVMGIQ  QENRQIREFQ  QENKELRTSL  EEHQSALELI
101  MSKYREQMFR  LLMASKKDDP  GIIMKLKEQH  SKIDMVHRNS  CEGFFLDASR
151  HILEAPQHGL  ERRHLEANQN  ELQAHVDQIT  EMAAVMRKAI  EIDEQQGCKE
201  QQRIFQLEQE  NKGLREILQI  TRESFLNLQK  DDASESTSLS  ALVTNSDLSL
251  RKS
```

SEQ ID NO: 4

*Figure 4*

WIT 3.0, A NOVEL GENE TO CONTROL SOFT TISSUE WOUND HEALING

BACKGROUND OF THE INVENTION

1. Field of Invention

This invention relates generally to the identification of a novel gene, Wit 3.0, and its use in wound healing. More particularly, the invention relates to methods and compositions of treatment including, but not limited to, adult skin wound healing, soft tissue wound healing and oral mucosa wound healing.

Specifically, the present invention identifies and describes Wit 3.0, a gene, differentially expressed in oral mucosa tissues undergoing wound healing.

The present invention also provides for methods of administering Wit 3.0 to incisional and/or excisional soft tissue wounds. Delivery of Wit 3.0 is in antisense form, or alternatively, in sense form.

2. Description of the Related Art

By definition, a wound disrupts the normal epithelial barrier, which is the first line of defense against invading microorganisms. Wound healing typically results after surgery or other injuries to the tissue and involves a complex set of cellular and molecular events to restore the structural integrity of the damaged tissue. Following injury or surgical incision, there are three main stages of wound repair. The initial phase occurs during the first 24 to 48 hours after the event and is characterized by blood coagulation, inflammation and initial wound closure. The middle phase occurs during the first week following the event, and is characterized by cell proliferation and formation of granulation tissue. Granulation tissue is described as small, red, grain-like prominences that form on raw surfaces such as that of wounds or ulcers. Granulations are processes of healing. This middle phase is dependent on new blood vessel formation, or angiogenesis. The last phase, occurring several weeks into the healing and repair process, is characterized by connective tissue synthesis and remodeling.

Fibroblasts in resting tissue are quiescent, immobile cells engaged in minimal biosynthetic activities. After wounding, these cell proliferative and migrate into the wound region where they synthesize and contract a new connective tissue matrix, including collagen, which resembles smooth muscle. Once healing is complete, the wound fibroblasts again become quiescent and regress through apoptosis.

Migration of fibroblasts to the injury site followed by fibroblast proliferation is stimulated by various growth factors (i.e., epidermal growth factor-EGF, fibroblast growth factor-FGF, transforming growth factor, TGF-beta). These factors also stimulate the synthesis and secretion of extracellular matrix components such as collagen and proteoglycans. At the same time, establishment of new blood vessels (angiogenesis) is occurring and stimulated by fibroblast growth factor (FGF) and vascular endothelial growth factor (VEGF).

As healing progresses there is a decrease in the number of active fibroblasts, an increase in extracellular matrix components such as collagen and a decrease in concentration of blood vessels. During this process, the region of the scar is immobilized and collagen fibers are deposited in a near-random fashion.

For example, healing of a clean, uninfected incision where the edges have been approximated with sutures begins when the edges fill with clotted blood. The blood clot at the surface becomes dehydrated forming a scab and within a day the epidermis thickens. A few days later, granulation tissue begins to occupy the incision space and fills it in a couple of days. In the event of larger incisions or wounds, there is an increase loss of cells and tissue at the injury site and wound contraction is mediated by myofibroblasts.

Therefore, the failure of these cellular and molecular events produces abnormal scarring. Examples of abnormal scarring include keloid formation, which is an accumulation of larger than normal amounts of collagen at the wound site creating a protruding scar; proud flesh, which is an abnormal increase in the amount of granulation tissue that blocks reepithelialization; contracture formation, which is immobilized tissue resulting in undesirable fixed, rigid scars that can limit normal range of motion; and fibrosis, which is abnormal connective tissue resulting from myofibroblast activity in the extended wound.

Other factors also undermine normal wound healing repair mechanisms. In particular, systemic disease, medications, and behavioral factors such as smoking and diet can impede the normal wound repair response. For example, diabetes and peripheral vascular disease impair the formation of healthy granulation tissue such as collagen. Medications such as immunosuppressants can inhibit the inflammatory response and delay wound healing. For example, corticosteroids are immunosuppressants that have dual effects: inhibiting lymphocyte function and inhibiting the synthesis of structural skin proteins, such as collagen.

It has been widely recognized that fetal skin and oral mucosa leave minimal scarring. The wound created in these tissues commonly exhibits the rapid initial wound closure likely due to the active approximation of the wound margin within the initial phase, or 24-48-hour period. In contrast, adult skin wounds do not close as rapidly as fetal skin and oral mucosa. It has also been postulated that the adult skin wound lacks initial wound closure mechanisms and tends to create excess tissue contraction and/or fibrosis formation in the later healing stages. Active approximation, similar to that of fetal skin and oral mucosa, in the adult can be achieved by placement of sutures. For example, well-sutured wounds have about 70% of the strength of normal skin. Although, minimal scarring has been observed in fetal skin and oral mucosa, to date, the molecular mechanisms involved in the fetal skin and oral mucosa wound closure have not been elucidated.

One-third of the elderly are currently edentulous (without teeth) in either one or both jaws. Formed as a result of wound healing, edentulous mucosa is the portion of the oral mucosa that covers the site where the tooth has been removed. The wound healing process during tooth extraction is thought to follow a similar chronological and physiological pattern as that of typical soft-tissue wound healing as previously discussed.

To maximize wound healing, growth factors and small peptides that stimulate the proliferation and biosynthetic activity of cells in the wound have to be isolated and characterized. Existing pharmaceutical creme formulations containing several different growth factors including platelet derived growth factor (PDGF) and transforming growth factor beta (TGFβ) do not ameliorate the situation occurring in the edentulous oral mucosa because the cremes originate from more than one cell type Another disadvantage of the existing formulations containing various growth factors is that the particular factor(s), which offer the greatest benefit in wound healing, cannot be specifically determined. Moreover, effects of multiple growth factors may be potentially adverse on distant organs. As a primary example, angiogenic growth factors enhance the proliferation of blood vessels and hence enhance wound repair. However, these same factors can also enhance neovascularization in areas where it is undesirable, such as accelerating the growth of any benign or malignant tumor.

Thus, an improved treatment is composed of an active agent, which is locally expressed at or near the region of the wound. Such an agent enhances wound healing at the local site of injury but is not deleterious to nearby normal healthy tissues.

Another improved treatment administers the active agent to minimize undesired effects on non-wound tissues. For example, a method of administration localizes and limits the active agent to restrict release of the factor to the wound site.

INVENTION SUMMARY

A general object of the present invention is to provide a method of treatment to improve wound healing and to minimize/prevent abnormal scarring caused by tissue contraction and fibrosis formation.

In accordance with one aspect of the present invention, these and other objectives are accomplished by providing a specific gene, Wit 3.0 alpha, or SEQ ID NO: 1 that is differentially expressed in wounded oral mucosa cells, relative to their decreased expression in non-wounded oral mucosa cells.

In accordance with another aspect of the present invention, these and other objectives are accomplished by providing a specific gene, Wit 3.0 beta, or SEQ ID NO: 3 that is differentially expressed in wounded oral mucosa cells, relative to their decreased expression in non-wounded oral mucosa cells.

In accordance with another aspect of the present invention, these and other objectives are accomplished by providing a method to treat soft tissue wound using anti-sense nucleic acid technologies.

In accordance with another aspect of the present invention, these and other objectives are accomplished by providing a method to treat soft tissue wound using sense nucleic acid technologies.

In accordance with another aspect of the present invention, these objectives are accomplished by providing a complimentary nucleic acid that has greater than 85% identity to the sequence of SEQ ID NO: 1 or to the sequence of SEQ ID NO: 3.

In accordance with another aspect of the present invention, these objectives are accomplished by providing a complimentary nucleic acid sequence that has greater than 85% identity to the sequence of SEQ ID NO: 1 or to the sequence of SEQ ID NO: 3 and further comprising an appropriate carrier.

In accordance with another aspect of the present invention, these objectives are accomplished by providing an amino acid sequence that has greater than 90% identity to the deduced amino acid sequence of SEQ ID NO: 1 gene, or to SEQ ID NO: 3.

In accordance with another aspect of the present invention, these objectives are accomplished by providing an amino acid sequence that has greater than 90% identity to the deduced amino acid sequence of SEQ ID NO: 1 gene, or to SEQ ID NO: 3 and further comprising an appropriate carrier.

In accordance with another aspect of the present invention, these objectives are accomplished by providing an expression vector, including but not limited to a CMV expression vector, containing the polynucleotide sequence that has greater than 85% identity to the sequence of SEQ ID NO: 1, or to the sequence of SEQ ID NO: 3.

In accordance with another aspect of the present invention, these objectives are accomplished by providing a genetically engineered host cell containing the expression vector further comprising of a polynucleotide sequence that has greater than 85% identity to the sequence of SEQ ID NO: 1, or to the sequence of SEQ ID NO: 3, said host cell is a prokaryotic cell or eukaryotic cell.

In accordance with another aspect of the present invention, these objectives are accomplished by providing a treatment to improve soft tissue wound healing using anti-sense nucleic acid technologies to reduce the up-regulation of SEQ ID NO: 1 and the SEQ ID NO: 1 encoding protein, and to SEQ ID NO: 3 and the SEQ ID NO: 3 encoding protein, and/or to a nucleotide sequence having greater than 85% identity to that of the sequence SEQ ID NO: 1 and/or SEQ ID NO: 3, thereby preventing soft tissue scar formation.

In accordance with another aspect of the present invention, these objectives are accomplished by providing a treatment to improve soft tissue wound healing using sense nucleic acid technologies to increase the synthesis of peptide encoded by SEQ ID NO: 1, or SEQ. ID NO: 3, and/or a nucleotide having greater than 85% identity to the sequence SEQ ID NO: 1, or SEQ. ID NO: 3, thereby encouraging the initial wound margin closure.

In accordance with another aspect of the present invention, these objectives are accomplished by providing a treatment to improve edentulous oral mucosa wound healing using sense nucleic acid technologies to increase the synthesis of peptide encoded by SEQ ID NO: 1, or SEQ. ID NO: 3, and/or a nucleotide having greater than 85% identity to the sequence SEQ ID NO: 1, or SEQ. ID NO: 3, thereby encouraging the initial wound margin closure.

The above described and many other features and attendant advantages of the present invention will become apparent from a consideration of the following detailed description when considered in conjunction with the accompanying drawings.

BRIEF DESCRIPTION OF THE DRAWINGS

Detailed description of the preferred embodiment of the invention will be made with reference to the accompanying drawings.

FIG. 1 is SEQ ID NO: 1, the nucleotide sequence of wound inducible transcript 3.0 alpha (Wit 3.0 alpha);

FIG. 2 is the deduced amino acid sequence (SEQ ID NO: 2) of SEQ ID NO: 1;

FIG. 3 is SEQ ID NO: 3, the nucleotide sequence of wound inducible transcript 3.0 beta (Wit 3.0 beta);

FIG. 4 is the deduced amino acid sequence (SEQ ID NO: 4) of SEQ ID NO: 3;

DETAILED DESCRIPTION OF THE PREFERRED EMBODIMENTS

Figures 5A, 5B:
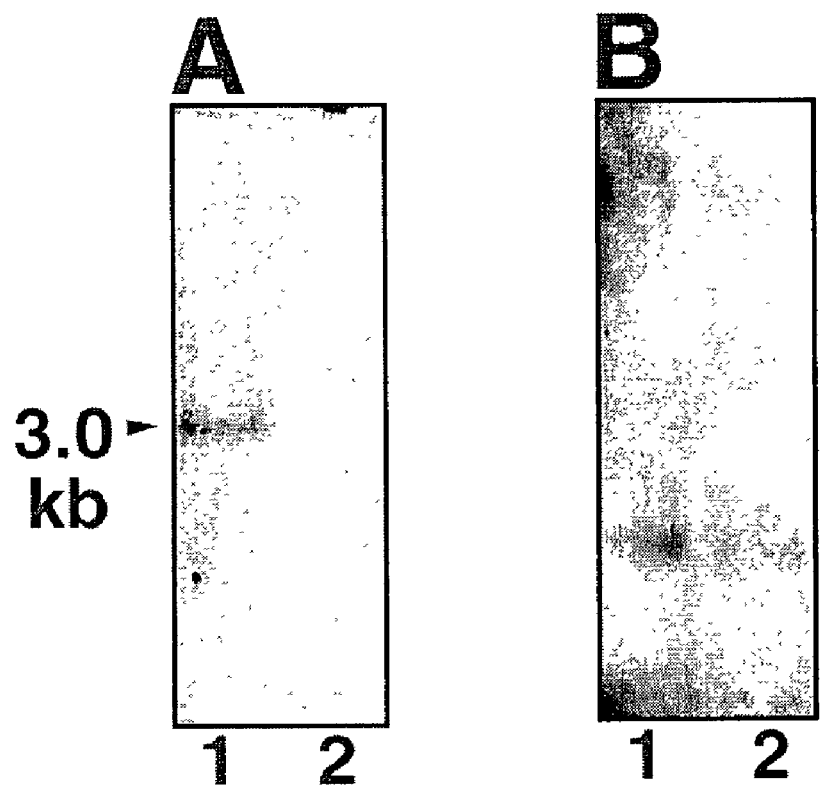
FIGS. 5A and 5B are Northern Blot analyses; 5A shows that SEQ ID NO: 1 DNA (Wit 3.0 alpha) hybridizes to an approximately 3.0 kb mRNA from edentulous oral mucosa tissue [lane 1], and does not hybridize to mRNA from gingival tissue [lane 2]; 5B is a Northern Blot control using glyceraldehyde-3-phosphate dehydrogenase (GAPDH) DNA.

This description is not to be taken in a limiting sense, but is made merely for the purpose of illustrating the general principles of the invention. The section titles and overall organization of the present detailed description are for the purpose of convenience only and are not intended to limit the present invention.

The edentulous oral mucosa wound rapidly contracts after tooth extraction. Despite the large wound size, tooth extraction does not create significant scarring in oral mucosa. However, unlike most other tissues undergoing repair, continued wound healing or wound contraction in the healing oral mucosa after tooth extraction may result in bone resorption of alveolar processes.

Thus, identifying a molecular marker which functions in mechanisms of wound healing, but at the same time does not have deleterious effects on nearby tissues, including but not limited to aveolar processes or bone tissue, enables improved treatment of the unique phenomenon occurring in the oral mucosa.

Wound Inducible Transcript 3.0 (Wit 3.0)

In the present invention, a novel gene, wound inducible transcript-3.0 (Wit 3.0), is isolated, identified and characterized from rat edentulous oral mucosa fibroblasts after tooth extraction. Two isoforms are characterized, Wit 3.0 alpha (SEQ ID NO: 1; FIG. 1) and Wit 3.0 beta (SEQ ID NO: 3; FIG. 3). The deduced amino acid sequence of Wit 3.0 alpha cDNA encodes a peptide that is 215 amino acids (SEQ ID NO: 2). Whereas the deduced amino acid sequence of Wit 3.0 beta encodes a peptide that is 253 amino acids (SEQ ID NO: 4). Both Wit 3.0 alpha and beta are isolated using a differential display polymerase chain reaction method, which allows for the identification of sequences derived from genes which are differentially expressed.

Briefly, using standard molecular techniques that are well known in the art, isolated RNA is reverse transcribed into single stranded cDNA. Then pairs of polymerase chain reaction (PCR) primers are used, which allows for the amplification of clones representing a random subset of the RNA transcripts within any given cell. PCR conditions are chosen to optimize amplified product yield and specificity including different lengths of primers, annealing and elongation temperatures and reaction times. The pattern of clones resulting from the reverse transcription and amplification of the mRNA of two different cell types is displayed via sequencing gel electrophoresis and compared. Finally, differences in the banding patterns of nucleic acids indicate potentially differentially expressed genes.

The present invention describes the full length of Wit 3.0 alpha and beta sequences (SEQ ID NO: 1 and SEQ ID NO: 3). However, polynucleotides with greater than 85% identity to SEQ ID NO: 1, and/or SEQ ID NO: 3, or any polypeptide or deduced amino acid with greater than 90% identity to SEQ ID NO: 1 and/or SEQ ID NO: 3 are features or principles of the present invention.

Identification, isolation and characterization of Wit 3.0 alpha and beta is also described in Sukotjo et al., and is hereby incorporated in its entirety by reference. Sukotjo et al. (2002)Molecular Cloning of the Wound Inducible Transcript (with 3.0) Differentially Expressed in Edentulous Oral Mucosa Undergoing Tooth Extraction Wound-Healing, *J. Dent. Res.* 81(4): 229-235.

Wit 3.0 Alpha is Localized to the Edentulous Oral Mucosa

Using the full-length Wit 3.0 alpha cDNA as a probe, Northern blot analysis shows that Wit 3.0 alpha is expressed in edentulous oral mucosa tissue, as shown in FIG. 5A, lane 1. The mRNA in edentulous oral mucosa tissue is approximately 3.0 kb in size (FIG. 5A, lane 1). In comparison, when the same Wit 3.0 cDNA probe is hybridized to a sample containing RNA from gingival tissue, there is no expression of the gene (FIG. 5A, lane 2). Thus, the Wit 3.0 alpha expression is specific to edentulous oral mucosa cells and not present from nearby gingival cells. To further determine the specificity of both probe and tissue for the presence of Wit 3.0 alpha, the same Northern blots as described in FIG. 5A are stripped and re-probed with a housekeeping gene, glyceraldehyde-3-phosphate dehydrogenase (GAPDH). FIG. 5B shows that GAPDH probe does not hybridize to a similar size RNA as the Wit 3.0 alpha probe.

Edentulous oral mucosa tissue samples are prepared by harvesting tissue post-tooth extraction and fixing the tissue by perfusion in 4% paraformaldehyde in phosphate buffer saline (PBS). Specimens are then prepared for histological staining and in situ hybridization by standard molecular biology techniques. Sense and antisense probes are prepared using Digoxigenin RNA labeling kit from Boehringer Mannheim (Indianapolis, Ind.). Color detection is performed using either hematoxylin and eosin or nitroblue tetrazolium (NBT). All specimens are examined under a light microscopy.

Figure 6:
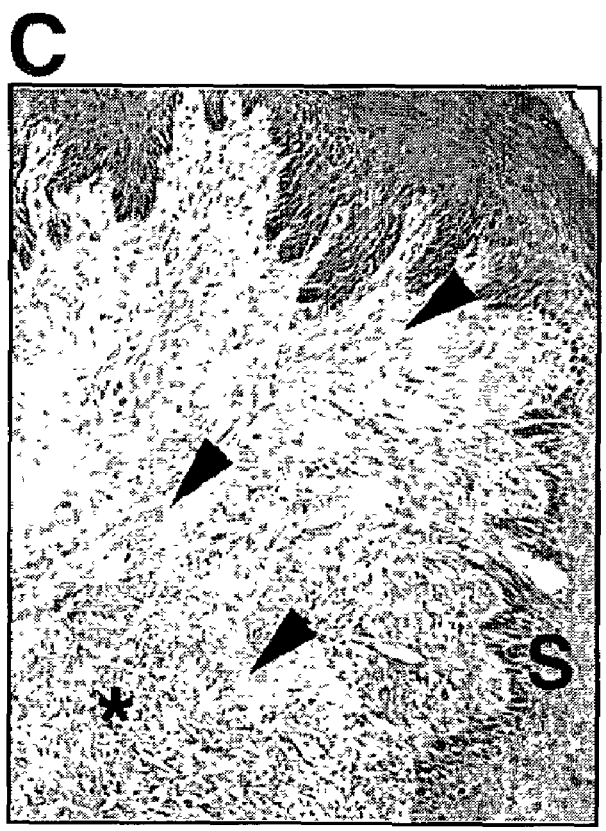
FIG. 6 is photomicrograph with an arrowhead representing the region of fibrosis connective tissue found next to the infiltrated inflammatory cells [*] adjacent to the extraction site [S]

FIG. 6 is a hematoxylin and eosin stain of post-extraction oral mucosa adjacent to the extraction socket (S). Epithelial proliferation and migration and active connective tissue re-organization are observed at the edge of the ruptured gingival. Arrowheads in FIG. 6 represent connective tissue fibrosis found next to the infiltrated immigrated cells (*) adjacent to the extraction socket (S).

Figure 7:
FIG. 7 is a photomicrograph of an in situ hybridization using SEQ ID NO: 1 DNA alpha (Wit 3.0 alpha)

FIG. 7 is positive in situ hybridization (arrows) is observed in fibroblasts adjacent to the extraction site, where dense fibrosis tissue is found adjacent to the extraction socket (S).

Wit 3.0 is Expressed in the Cytoplasm

To study the functions of Wit 3.0 alpha, a recombinant cloning plasmid is constructed using a cytomegalovirus (CMV) expression vector (pCMV-2). The correct Wit 3.0 alpha open reading frame is positioned downstream from the CMV promoter. NIH3T3 fibroblast cells are then transfected with the recombinant CMV plasmid.

Figures 8A, 8B:
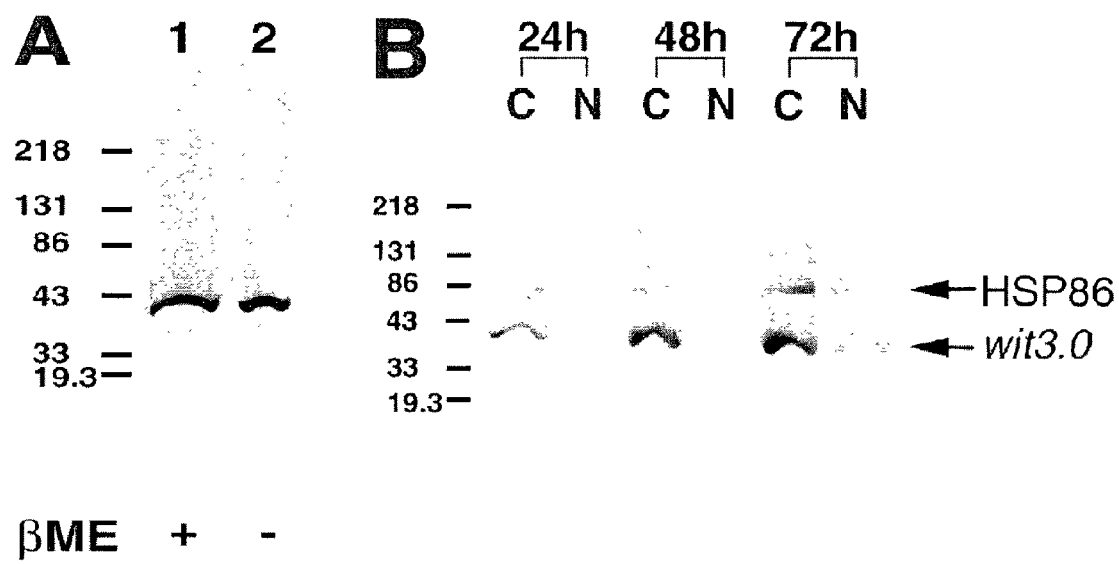
FIGS. 8A and 8B are Western Blots using various fractions of NIH3T3 fibroblasts transfected with SEQ ID NO: 1 DNA (Wit 3.0).

An approximately 40 KDa protein is observed in NIH3T3 fibroblastic cells transfected with the CMV recombinant plasmid as shown in Western blot analysis in FIG. 8A. Furthermore, Wit 3.0 alpha does not contain any deducible disulfide bonding, since samples treated with (FIG. 8A, lane 1) and without (FIG. 8A, lane 2) the presence of beta-mercaptoethanol showed no change in the molecular weight of the protein. Wit 3.0 alpha is predominantly localized in the cytoplasm (C) and not in the nucleus (N) (refer to FIG.

8B). Also, the protein in the cytoplasm (C) is the same predicted protein size (FIG. 8B) as that found in the total cell fractions (FIG. 8A).

Although the present invention has been described in terms of the preferred embodiment above, numerous modifications and/or additions to the above-described preferred embodiments would be readily apparent to one skilled in the art.

For example, the present invention describes the full length polynucleotide of Wit 3.0 alpha and beta, or SEQ ID NO: 1 and SEQ ID NO: 3, respectively, in operative association with a CMV nucleotide regulatory element to control expression of a polynucleotides with greater than 85% identity to SEQ ID NO: 1 and/or SEQ ID NO: 3. Polynucleotides complementary to greater than 85% identity to SEQ ID NO: 1, and/or SEQ ID NO: 3 and in operative association with other nucleotide regulatory elements controlling greater than 85% identity SEQ ID NO: 1 and/or SEQ ID NO: 3 expression are features or principles of the present invention.

Collagen Contraction Assays

Figure 9A:
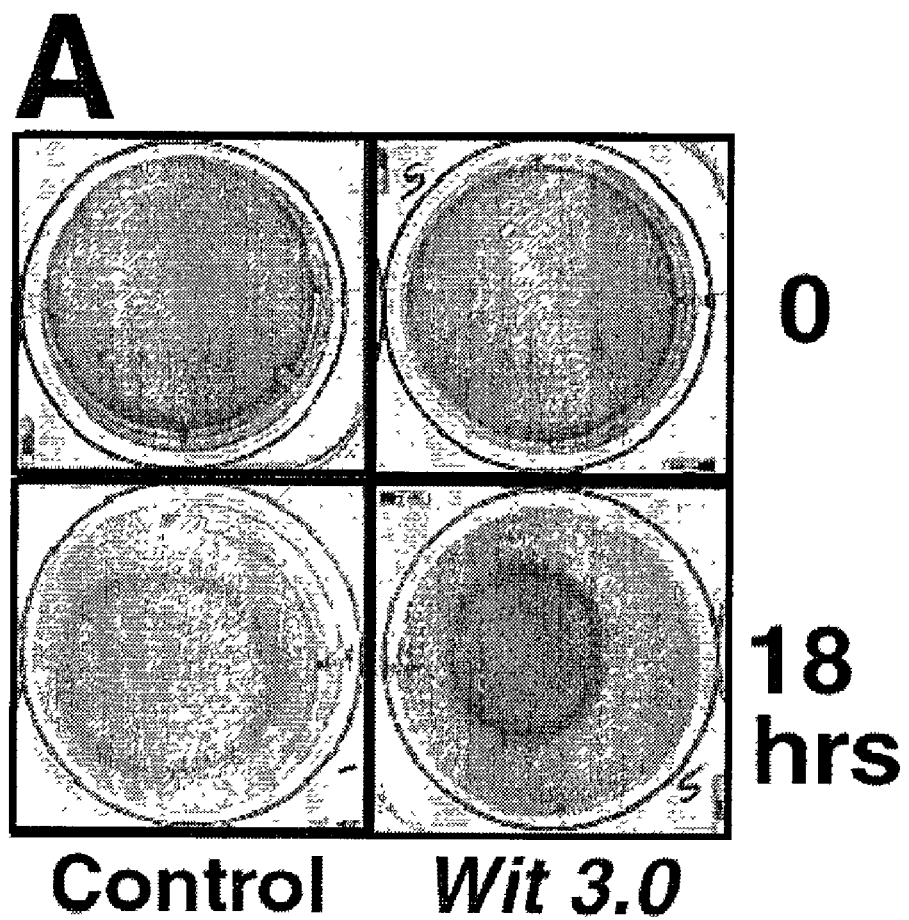
FIG. 9A is a photomicrograph showing collagen gel contraction by control NIH3T3 fibroblast and NIH3T3 transfected with expression plasmid containing SEQ ID NO: 1 DNA (Wit 3.0)

In the present invention, collagen gel contraction is used to assay for collagen contraction. In vitro collagen gel contraction assays are widely used to model wound contraction in vivo. For example, fibroblasts in collagen gel suspensions undergo cell-mediated contraction of the gel to form a three-dimensional, tissue—like structure. As shown in FIG. 9A, contraction of the collagen actually pulls the matrix away from the petri dish, or container. This contraction mechanism mimics wound contraction in vivo.

Interestingly, oral mucosal fibroblasts show faster contraction rates as compared with other types of fibroblasts, including dermal fibroblasts during the first 12-24 hours in culture. Additionally, oral mucosal fibroblasts contract faster with or without TGF-β1, a wound healing promoting factor. Hence, there are other wound healing promoting factor(s), or active agent(s), within oral mucosal fibroblasts.

By way of example, but not limitation, the following encompasses one or more embodiments of the invention. It is to be understood that the invention is not limited to these specific embodiments.

EXAMPLE 1

Determining the Function of Wit 3.0 in Wound Contraction using Collagen Gel Contraction Assays.

NIH3T3 cells are transfected with the Wit 3.0 alpha recombinant CMV plasmid and suspended in a collagen gel matrix. A similar experiment is performed using NIH3T3 cells not harboring the Wit 3.0 alpha CMV recombinant plasmid. NIH3T3 cells transfected with Wit 3.0 alpha CMV recombinant plasmid show rapid collagen gel contraction compared to untransfected NIH3T3 cells after 18 hours (FIG. 9A). To determine the periods when collagen contraction is most effective over a 36-hour period, periodic data is collected from the collagen gel contraction assays.

Figure 9B:
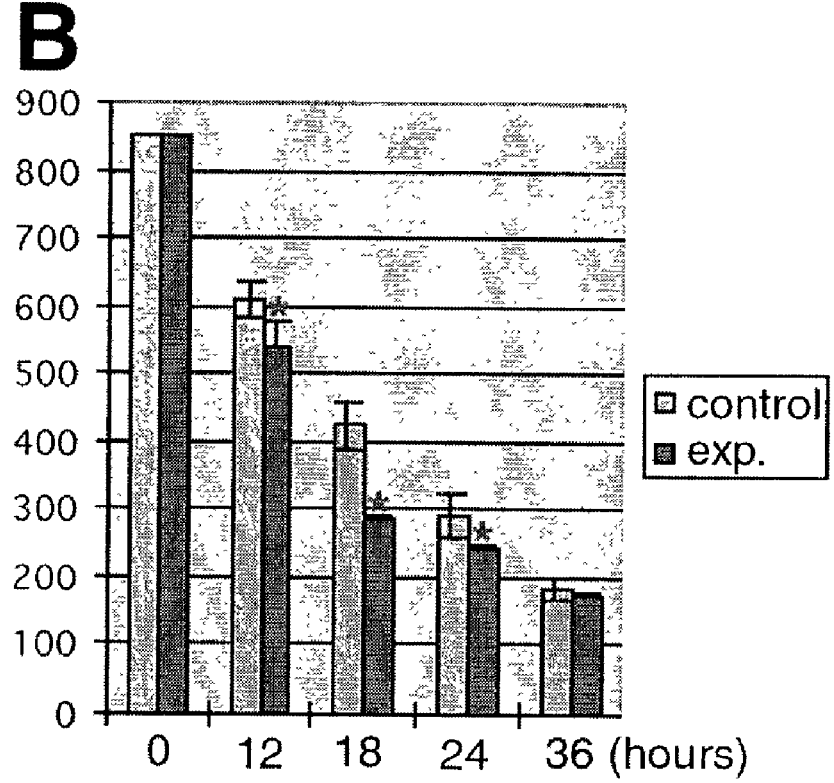
FIG. 9B is a bar graph assessing contraction of collagen gel by NIH3T3 fibroblasts with and without SEQ ID NO: 1 DNA (Wit 3.0).

FIG. 9B is a bar graph comparing the collagen gel contraction assays for transfected and untransfected NIH3T3 cells. Interestingly, during the first 24 hours, transfected NIH3T3 cells with Wit 3.0 alpha show significantly accelerated collagen gel contraction in vitro ($p<0.05$). Thus, increased rates of collagen gel contraction in vitro mimic normal connective tissue repair post injury in vivo.

In summary, these results suggest that in vitro, Wit 3.0 alpha is involved in the soft tissue wound healing through putative wound contraction. Wit 3.0 alpha further provides a novel clue to elucidate the molecular mechanism of initial wound margin approximation critical to scarless wound healing.

EXAMPLE 2

Determining the Efficiency of Gene Delivery Systems to Oral Mucosa Fibroblasts.

One of the major challenges in therapeutic gene delivery is to deliver specific genes to the targeted tissues and cells and to control the duration of gene expression. It is well known that the application of "naked DNA" is an effective alternative in treating chronic diseases. Introduction of naked DNA and RNA sequences into a mammal, including humans, to achieve controlled expression of the polypeptide is useful in, but not limited to, gene therapy.

Previously, it has been shown that plasmid gene transfer can be achieved using a collagen gel delivery system. This delivery system is appropriate for schemes involving tooth extraction wound healing and/or residual ridge augmentation surgery.

EXAMPLE 3

Examining the Effect of Wit 3.0 Anti-Sense and Sense Nucleic Acid Containing Expression Vectors on in vitro Collagen Gel Contraction using Rat Oral Mucosa Fibroblasts.

It has been shown that expression of Wit 3.0 alpha increases in oral mucosa cells during tooth extraction wound healing (FIG. 5A and FIG. 7). Moreover, fibroblasts derived from the wound site also exhibit the elevated steady state level of Wit 3.0 mRNA as compared to fibroblasts from the untreated site (FIG. 5A); see Sukotjo et al.

Anti-sense recombinant plasmid construction. An expression vector construct containing the anti-sense sequence of the correct open reading frame of Wit 3.0 alpha is generated in pFLAG-CMV2 (Sigma, St. Louis, Mo.). The construct is sequenced to determine and confirm proper orientation. The sense expression vector construct containing Wit 3.0 alpha is also generated similarly; see Sukotjo et al.

Isolating edentulous oral mucosa fibroblasts. Sprague-Dawley rats (male, 40 days old) are anesthetized by intramuscular injection with 12.96 mg/100 g body weight ketamine (Fort Dodge Laboratory. Inc., Fort Dodge, Iowa) and 1.44 mg/100 g body weight xylazine (Miles Inc., Shannee Mission, Kans.). Extractions of maxillary right molars are performed with a dental explorer on a custom-made surgical bed (Nishimura et al., 1987). After a 7 day-healing period, the animals are sacrificed and the healing edentulous oral mucosa and contralateral untreated gingival are harvested and separately disaggregated by clostridium histolyticum A collagenase (1 mg/ml, Boehringer Mannheim, Germany). Fibroblast cultures are maintained as described above; see Sukotjo et al.

In vitro gene delivery. Fibroblasts derived from edentulous oral mucosa and normal gingiva are mixed at a concentration of $1.5 \times 10^5$ cells/ml at 4° C. into the collagen gel containing the optimal concentration of the anti-sense expression vector, the sense expression vector, the control vector or no plasmid DNA. The cells in collagen gel are cultured into 6 well plates.

Collagen gel contraction assay. Collagen gel cell cultures are monitored every 6 hours by taking standardized photographs. After 124 hours the cultures are terminated. The photographs are digitized and the diameter/area of the collagen gel is measured (ImagePro Plus).

EXAMPLE 4

Testing the Effect of Wit 3.0 Gene Therapy on the Oral Mucosa Contraction in the Rat Tooth Extraction Model Experimental Procedures for Anti-sense gene therapy. The present invention is also directed to a method of gene therapy by covalent bonding formation between interstrand nucleotide sequences, particularly between certain specific Wit 3.0 alpha transcript and its anti-sense probe described above.

Since covalently bonded intracellular transcripts are not available for translation, the present invention can be used to inhibit protein synthesis. For example, if the concentration of the anti-sense probe is too high in transfected cells, the probe will covalently bind not only to the targeted gene transcript but also to its genomic homologous region, resulting in no replication of the transfected cells. In contrast, if the concentration is too low, the probe will not sufficiently block most of the gene transcript, resulting in reduced levels to zero levels of inhibition of translation. Thus, the optimal concentration will vary depending on the transcriptional activity of specific genes in specific cells.

This method is primarily designed for inhibiting a specific gene expression in cells. The method of gene therapy using covalent binding of an anti-sense probe to its homologous transcript has been previously described in U.S. Pat. No. 6,015,676 to Lin et al., (2000), which is hereby incorporated in its entirety by reference.

Briefly, a preferred embodiment of the present invention is based on: 1) Single-stranding of probe sequences as anti-sense; 2) Marking two reference points prior to tooth extraction; 3) Introduction of anti-sense probes into the mammal with a delivery carrier such as gene activated matrix (GAM); 4) in-cell-hybridization of the anti-sense probes with targeted gene transcript(s) to form covalent bonding within some specific base-pairs; and 5) assessing the effect of gene therapy by measuring the distance between the two reference points.

Examples as mentioned here are developed into continuity in part of the present invention and are not intended in any way to limit the broad features or principles of the present invention.

In summary, it is noted that specific illustrative embodiments of the invention have been disclosed hereinabove. However, it is to be understood that the invention is not limited to these specific embodiments or examples.

In one preferred embodiment of the present invention nucleic acid molecules with greater than 85% identity to SEQ ID NO: 1 and/or SEQ ID NO: 3 are provided.

In another preferred embodiment, similarity searches are based on processes of aligning a query sequence (Wit 3.0) with every sequence in a database and calculating for the quality of each alignment. The present invention performs similarity searches using the heuristic program called basic alignment search tool or BLAST. BLAST expectation values (E values) or scores smaller than 0.05 or 0.02 are considered significant.

Moreover, certain amino acid substitutions, entitled "conservative" amino acid substitutions, can frequently be made in a protein or a peptide without altering either the conformation or the function of the protein or peptide. Therefore, one embodiment of the present invention, includes changes for substituting any of isoleucine (I), valine, and leucine (L) for any other of these amino acids; aspartic acid (D) for glutamic acid (E) and vice versa; glutamine (Q) for asparagine (N) and vice versa; and serine for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine. Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Cysteine (C) can frequently be replaced by serine when cysteine's capacity to form disulfide bond is either undesirable or unneeded. Still other changes can be considered "conservative" in particular environments.

In one preferred embodiment, polypeptides that are greater than 85% identity to the polypeptide encoded by SEQ ID NO: 1 and/or SEQ ID NO: 3 are provided.

In another preferred embodiment, nucleic acid molecules, preferably DNA molecules that hybridize to and are therefore the complements of, the DNA sequence of SEQ ID NO: 1 and/or SEQ ID NO: 3, or to greater than 85% identity to SEQ ID NO: 1 and/or SEQ ID NO: 3 are provided.

These nucleic acid molecules may act as target gene antisense molecules, useful, for example, in target gene regulation. In one preferred embodiment of the present invention, antisense nucleotides are phosphodiester oligodeoxynucleotides. However, other nucleotides including nonionic methylphosphonate oligonucleotide analogs, phosphorothioates, phosphorodithioates, phosphoramidate and peptide nucleic acids (PNAs) may be used. Smith et al., 1986, Antiviral effect of an oligo (nuleoside methylphosphonate) complementary to the splice junction of herpes simplex virus type 1 immediate early pre-mRNAs 4 and 5, *Proc. Natl., Acad. Sci.* 83: 2787-2791; Eckstein, F., 1991, Phosphorothioates in molecular biology, *Trends in Biol. Sci.,* 14:97-100; Caruthers, M. H., 1985, Gene synthesis machines: DNA chemistry and its uses, *Science,* 230: 281-285. Further, in one preferred embodiment, these nucleic acid molecules may act to encourage the initial wound margin closure by providing a treatment to improve soft tissue wound healing using sense nucleic acid technologies to increase the synthesis of peptide encoded by SEQ ID NO: 1 and/or SEQ ID NO: 3.

In another preferred embodiment, other sequences may be identified and isolated in other species without undue experimentation by using standard molecular biology techniques well known in the art.

In another preferred embodiment, there may exist other genes at other genetic loci within the genome that encode proteins, which have extensive identity to one or more domains of the gene sequence SEQ ID NO: 1 and/or SEQ ID NO: 3. These genes may be identified by similar molecular biology techniques.

Accordingly, the invention is not limited to the precise embodiments described in detail hereinabove.

While the specification describes particular embodiments of the present invention, those of ordinary skill can devise variations of the present invention without departing from the inventive concept.

SEQUENCE LISTING

<160> NUMBER OF SEQ ID NOS: 4

<210> SEQ ID NO 1
<211> LENGTH: 2746
<212> TYPE: DNA
<213> ORGANISM: artificial sequence
<220> FEATURE:
<223> OTHER INFORMATION: rattus norvegicus
<220> FEATURE:
<221> NAME/KEY: misc_feature
<222> LOCATION: (2030)..(2030)
<223> OTHER INFORMATION: n is any naturally occurring nucleotide

<400> SEQUENCE: 1

| | | | | | |
|---|---|---|---|---|---|
| acgcggggga | agtctcgcga | ggcttgtcgc | tgtgtggctg | ccagtagcgg | aggttctggt | 60 |
| ccgcccggga | tggagccgag | gcaagcgggc | tgccggatcc | tccctgccgc | tgtgtgagca | 120 |
| gggctgtgcg | tccgctcgct | gagcaggcgc | agcgaggccg | cggagagcac | tctctgggcg | 180 |
| cctccatctc | gcgggtggtg | gtcgccgtct | ctgacggctg | aggggactg | aagctgagtg | 240 |
| gaaaaacacg | agtgggtgaa | cctctgagcc | gggctccctg | tctccgtgct | ctcactgagc | 300 |
| tcctgccggg | aacagagaaa | tgagctgcac | cattgagaag | gcacttgctg | atgctaaggc | 360 |
| ccttgttgaa | cggttgagag | accatgatga | tgcagcagag | tctctcatcg | aacagaccac | 420 |
| tgccctcagc | aagcgagtgg | aagccatgaa | acagtatcag | gaagaaatcc | aagaacttaa | 480 |
| tgaagtagca | agacatcggc | cacgatccac | actagttatg | ggaatccagc | aagaaaacag | 540 |
| acaaatcaga | gaattccaac | aagagaacaa | agaactgcgc | acatccttgg | aagagcacca | 600 |
| gtctgccttg | gaactgataa | tgagcaagta | tcgagagcag | atgttcagat | tgctaatggc | 660 |
| cagcaagaag | gacgacccgg | gcataataat | gaagttaaag | gagcagcact | caaaggagtt | 720 |
| gcaagcacat | gttgaccaga | tcaccgagat | ggcagcagta | atgagaaaag | ctattgaaat | 780 |
| tgacgaacag | cagggttgca | aggaacagca | gcgcatattt | caacttgaac | aagaaaacaa | 840 |
| aggcttgaga | gagatccttc | agataactcg | agaatccttt | ttgaaccttc | agaaggatga | 900 |
| tgcgtcagag | agtacatctc | tgtccgcctt | agtgactaac | agtgacctga | gtctgaggaa | 960 |
| gagctgagtg | gttggctgag | gtcactaaga | cgggcccagg | agtgagtgga | tggatgaaca | 1020 |
| taaacccaac | tccagtcagc | ctcttttcctc | tagtatgtca | ggggcactgg | cgaagagaca | 1080 |
| gtagcaggat | gtatagccag | tggtcataaa | ctagatccca | gtcacagctc | gacaggaaaa | 1140 |
| cctgggccac | agagtgaaca | ttgagtctcc | aaggtgctgc | tgaggactgc | aatttgagaa | 1200 |
| gtgctgttgg | cctcttggat | gagatatggg | tcaccctgaa | tgctcctaat | aaacgtcgga | 1260 |
| aagcctaaat | tatcacaact | ccaaaagaag | gttggtgtgg | tgttctggat | ggaagacttt | 1320 |
| gttctgattc | ctgtccttct | gttcagtgtc | agagtcagca | tagcttatgt | atgtaccgct | 1380 |
| tctgtctcgg | tgctcccatc | cccctgccca | tctgttcatc | gccggcagtt | cacatttaca | 1440 |
| ggctatagga | atatgtcact | cgcatcacaa | actgaagaaa | ggaatatact | tgcacctagt | 1500 |
| tcccataact | cttaactagc | aagttattcg | tgacttgctt | gagtatatgt | acctcaggaa | 1560 |
| ggaaggaaag | acaagaatat | actttctaag | aaagacagtt | ttatatagac | acatttagta | 1620 |
| ggttaaacta | ctttgagaga | ctatgtttgg | ttctctgtta | acaatgagcc | tggctcttcc | 1680 |
| tcctctctac | atgatgttta | aggatacagg | acagaggggt | tggggattta | gctcagtggt | 1740 |
| agagcgcttg | cctagcaacc | gcaaggccct | gggttcggtc | cccagctcct | aaaaaaaggg | 1800 |
| aaaaaaaaaa | ggatacagga | tagctcacta | gtacacagag | ttggcatatt | taatgtaata | 1860 |

-continued

```
agataggtat ggtcatttcc aagtaaattt ggaattcttt ggtatttaaa aaaacacctc    1920
ttcaaacata taagtaagaa agcaggctcc aaaatcaaag ttctgggact gagtctaaac    1980
cctgtttagt tcttataacc tgtgattttt ccctacaacc tgtgactcan aaactggcag    2040
tgaaagtgtg ggcccacagg cattgtgctt tgcactttaa aaaaaaaaaa gcttaagacc    2100
acaagataga gaagtgtgct ttaataccat tgcagcctaa actcttctgt agtgatcaga    2160
ataaaagaat aaaagattgt gaaatacggc aaaaaatata caatacttgt atgtgaagtt    2220
agcacagata aaaagtaaat catttgtaag tacatattac tttgcagtgt aattttatgt    2280
gtaatttcat gtattggcaa aattcatagg acttttactt gagaaccttt cattctgaag    2340
tttgaggtga gtggggtcat aggtcaggta ggaaagggcc agtacccag gtgataaacc     2400 gttgtcatgc agaggcctta atatttata tttaggtgaa tttatttcta agacttttct     2460
attggttctg ggagagtgtc ccttagttta gtggtcattc tttcatgtag tttggctcca    2520
ggccagaatc ttagaagaaa ggctacacag ttgagatgag gcagaatcaa ggagtgagta    2580
gttctattgt gaaatgttat ttcagaagta attatttta taaaaaaatt atttactctt     2640
tgtcttcttg gatataagtt taaggttgtg aatattgaaa gacatttgca ttgttcttag    2700
caagttttcc atccctccta tcaccccccc cctaaaaaaa aaaaaa                   2746
```

```
<210> SEQ ID NO 2
<211> LENGTH: 195
<212> TYPE: PRT
<213> ORGANISM: artificial sequence
<220> FEATURE:
<223> OTHER INFORMATION: wit 3.0 alpha translated peptide sequence

<400> SEQUENCE: 2

Met Ser Cys Thr Ile Glu Lys Ala Leu Ala Asp Ala Lys Ala Leu Val
1               5                   10                  15

Glu Arg Leu Arg Asp His Asp Asp Ala Ala Glu Ser Leu Ile Glu Gln
            20                  25                  30

Thr Thr Ala Leu Ser Lys Arg Val Glu Ala Met Lys Gln Tyr Gln Glu
        35                  40                  45

Glu Ile Gln Glu Leu Asn Glu Val Ala Arg His Arg Pro Arg Ser Thr
    50                  55                  60

Leu Val Met Gly Ile Gln Gln Glu Asn Arg Gln Ile Arg Glu Phe Gln
65                  70                  75                  80

Gln Glu Asn Lys Glu Leu Arg Thr Ser Leu Glu Glu His Gln Ser Ala
                85                  90                  95

Leu Glu Leu Ile Met Ser Lys Tyr Arg Glu Gln Met Phe Arg Leu Leu
            100                 105                 110

Met Ala Ser Lys Lys Asp Asp Pro Gly Ile Ile Met Lys Leu Lys Glu
        115                 120                 125

Gln His Ser Lys Glu Leu Gln Ala His Val Asp Gln Lys Glu Gln Glu
    130                 135                 140

Arg Ile Phe Gln Leu Glu Gln Glu Asn Lys Gly Leu Arg Glu Ile Leu
145                 150                 155                 160

Gln Ile Thr Arg Glu Ser Phe Leu Asn Leu Gln Lys Asp Asp Ala Ser
                165                 170                 175

Glu Ser Thr Ser Leu Ser Ala Leu Glu Thr Asn Ser Thr Leu Ser Leu
            180                 185                 190

Arg Lys Ser
        195
```

<210> SEQ ID NO 3
<211> LENGTH: 762
<212> TYPE: DNA
<213> ORGANISM: artificial sequence
<220> FEATURE:
<223> OTHER INFORMATION: rattus norvigicus

<400> SEQUENCE: 3

| | | | | | |
|---|---|---|---|---|---|
| atgagctgca | ccattgagaa | ggcacttgct | gatgctaagg | cccttgttga | acggttgaga | 60 |
| gaccatgatg | atgcagcaga | gtctctcatc | gaacagacca | ctgccctcag | caagcgagtg | 120 |
| gaagccatga | acagtatca | ggaagaaatc | caagaactta | tgaagtagc | aagacatcgg | 180 |
| ccacgatcca | cactagttat | gggaatccag | caagaaaaca | gacaaatcag | agaattccaa | 240 |
| caagagaaca | agaactgcg | cacatccttg | gaagagcacc | agtctgcctt | ggaactgata | 300 |
| atgagcaagt | atcgagagca | gatgttcaga | ttgctaatgg | ccagcaagaa | ggacgacccg | 360 |
| ggcataataa | tgaagttaaa | ggagcagcac | tcaaagattg | acatggtaca | tcgtaacagc | 420 |
| tgcgaaggat | tcttcctgga | tgcatctcgg | cacatccttg | aagcacctca | gcacggactg | 480 |
| gagaggaggc | acttggaagc | aaatcagaat | gagttgcaag | cacatgttga | ccagatcacc | 540 |
| gagatggcag | cagtaatgag | aaaagctatt | gaaattgacg | aacagcaggg | ttgcaaggaa | 600 |
| cagcagcgca | tatttcaact | tgaacaagaa | aacaaaggct | tgagagagat | ccttcagata | 660 |
| actcgagaat | ccttttgaa | ccttcagaag | gatgatgcgt | cagagagtac | atctctgtcc | 720 |
| gccttagtga | ctaacagtga | cctgagtctg | aggaagagct | ga | | 762 |

<210> SEQ ID NO 4
<211> LENGTH: 253
<212> TYPE: PRT
<213> ORGANISM: artificial sequence
<220> FEATURE:
<223> OTHER INFORMATION: wit 3.0 beta translated peptide sequence

<400> SEQUENCE: 4

Met Ser Cys Thr Ile Glu Lys Ala Leu Ala Asp Ala Lys Ala Leu Val
1               5                   10                  15

Glu Arg Leu Arg Asp His Asp Asp Ala Ala Glu Ser Leu Ile Glu Gln
            20                  25                  30

Thr Thr Ala Leu Ser Lys Arg Val Glu Ala Met Lys Gln Tyr Gln Glu
        35                  40                  45

Glu Ile Gln Glu Leu Asn Glu Val Ala Arg His Arg Pro Arg Ser Thr
    50                  55                  60

Leu Val Met Gly Ile Gln Gln Glu Asn Arg Gln Ile Arg Glu Phe Gln
65                  70                  75                  80

Gln Glu Asn Lys Glu Leu Arg Thr Ser Leu Glu Glu His Gln Ser Ala
                85                  90                  95

Leu Glu Leu Ile Met Ser Lys Tyr Arg Glu Gln Met Phe Arg Leu Leu
            100                 105                 110

Met Ala Ser Lys Lys Asp Asp Pro Gly Ile Ile Met Lys Leu Lys Glu
        115                 120                 125

Gln His Ser Lys Ile Asp Met Val His Arg Asn Ser Cys Glu Gly Phe
    130                 135                 140

Phe Leu Asp Ala Ser Arg His Ile Leu Glu Ala Pro Gln His Gly Leu
145                 150                 155                 160

Glu Arg Arg His Leu Glu Ala Asn Gln Asn Glu Leu Gln Ala His Val
                165                 170                 175

-continued

```
Asp Gln Ile Thr Glu Met Ala Ala Val Met Arg Lys Ala Ile Glu Ile
            180                 185                 190

Asp Glu Gln Gln Gly Cys Lys Glu Gln Glu Arg Ile Phe Gln Leu Glu
        195                 200                 205

Gln Glu Asn Lys Gly Leu Arg Glu Ile Leu Gln Ile Thr Arg Glu Ser
    210                 215                 220

Phe Leu Asn Leu Gln Lys Asp Asp Ala Ser Glu Ser Thr Ser Leu Ser
225                 230                 235                 240

Ala Leu Glu Thr Asn Ser Thr Leu Ser Leu Arg Lys Ser
                245                 250
```

We claim:

1. An isolated nucleic acid molecule consisting of a polynucleotide having a nucleotide sequence selected from the group consisting of:
   (a) the nucleotide sequence of SEQ ID NO:3;
   (b) a nucleotide sequence encoding the amino acid sequence of SEQ ID NO:4; and
   (c) the nucleic acid sequence that is complementary to the nucleic acid sequence of SEQ ID NO:3.

2. The isolated nucleic acid molecule of claim 1, wherein the nucleic acid is DNA.

3. The isolated nucleic acid molecule of claim 1, wherein the nucleic acid is cDNA.

4. The isolated nucleic acid molecule of claim 1, wherein the nucleic acid is RNA.

5. An isolated nucleic acid molecule which encodes the amino acid sequence of SEQ ID NO: 4.

6. An expression vector comprising a nucleic acid molecule and control elements for expression of the nucleic acid molecule in a suitable host cell wherein the nucleic acid molecule encodes the amino acid sequence of SEQ ID NO:4.

7. An isolated host cell comprising the expression vector of claim 6.

8. The host cell of claim 7, wherein the cell is a eukaryotic cell.

9. The host cell of claim 7, wherein the cell is a procaryotic cell.

10. A composition comprising:
    (a) an isolated nucleic acid molecule of claim 1; and
    (b) a carrier.

11. The composition of claim 10, wherein the carrier is an organic matrix including collagen gel or synthetic matrix.

* * * * *

UNITED STATES PATENT AND TRADEMARK OFFICE
CERTIFICATE OF CORRECTION

| | |
|---|---|
| PATENT NO. | : 7,365,175 B2 |
| APPLICATION NO. | : 10/170786 |
| DATED | : April 29, 2008 |
| INVENTOR(S) | : Nishimura et al. |

It is certified that error appears in the above-identified patent and that said Letters Patent is hereby corrected as shown below:

Please replace the Sequence Listing with the following Sequence Listing.

```
                      SEQUENCE LISTING

<110> Nishimura, Ichiro
         Sukotjo, Cortino
         The Regents of the University of California <120> Wit 3.0, a Novel Gene to Control Soft Tissue Wound
         Healing

<130> 02307K-170510US

<140> US 10/170,786
   <141> 2002-06-12

<150> US 60/297,720
   <151> 2001-06-12

<160> 4

<170> PatentIn Ver. 2.1

<210> 1
   <211> 2746
   <212> DNA
   <213> Rattus sp.

<220>
   <221> CDS
   <222> (320)..(967)
```

UNITED STATES PATENT AND TRADEMARK OFFICE
CERTIFICATE OF CORRECTION

PATENT NO. : 7,365,175 B2
APPLICATION NO. : 10/170786
DATED : April 29, 2008
INVENTOR(S) : Nishimura et al.

It is certified that error appears in the above-identified patent and that said Letters Patent is hereby corrected as shown below:

```
<223> wound inducible transcript 3.0 alpha (Wit 3.0
      alpha)

<220>
<221> modified_base
<222> (2030)
<223> n = g, a, c or t

<400> 1
acgcggggga agtctcgcga ggcttgtcgc tgtgtggctg ccagtagcgg aggttctggt  60
ccgcccggga tggagccgag gcaagcgggc tgccggatcc tccctgccgc tgtgtgagca 120
gggctgtgcg tccgctcgct gagcaggcgc agcgaggccg cggagagcac tctctgggcg 180
cctccatctc gcgggtggtg gtcgccgtct ctgacggctg aggggactg aagctgagtg 240 gaaaaacacg agtgggtgaa cctctgagcc gggctccctg tctccgtgct ctcactgagc 300
tcctgccggg aacagagaa atg agc tgc acc att gag aag gca ctt gct gat 352
                     Met Ser Cys Thr Ile Glu Lys Ala Leu Ala Asp
                      1               5                      10 gct aag gcc ctt gtt gaa cgg ttg aga gac cat gat gat gca gca gag 400
Ala Lys Ala Leu Val Glu Arg Leu Arg Asp His Asp Asp Ala Ala Glu
             15                  20                  25 tct ctc atc gaa cag acc act gcc ctc agc aag cga gtg gaa gcc atg 448
Ser Leu Ile Glu Gln Thr Thr Ala Leu Ser Lys Arg Val Glu Ala Met
         30                  35                  40 aaa cag tat cag gaa gaa atc caa gaa ctt aat gaa gta gca aga cat 496
Lys Gln Tyr Gln Glu Glu Ile Gln Glu Leu Asn Glu Val Ala Arg His
     45                  50                  55 cgg cca cga tcc aca cta gtt atg gga atc cag caa gaa aac aga caa 544
Arg Pro Arg Ser Thr Leu Val Met Gly Ile Gln Gln Glu Asn Arg Gln
 60                  65                  70                  75 atc aga gaa ttc caa caa gag aac aaa gaa ctg cgc aca tcc ttg gaa 592
Ile Arg Glu Phe Gln Gln Glu Asn Lys Glu Leu Arg Thr Ser Leu Glu
             80                  85                  90 gag cac cag tct gcc ttg gaa ctg ata atg agc aag tat cga gag cag 640
Glu His Gln Ser Ala Leu Glu Leu Ile Met Ser Lys Tyr Arg Glu Gln
         95                  100                 105
```

UNITED STATES PATENT AND TRADEMARK OFFICE
CERTIFICATE OF CORRECTION

PATENT NO. : 7,365,175 B2
APPLICATION NO. : 10/170786
DATED : April 29, 2008
INVENTOR(S) : Nishimura et al.

It is certified that error appears in the above-identified patent and that said Letters Patent is hereby corrected as shown below:

```
atg ttc aga ttg cta atg gcc agc aag aag gac gac ccg ggc ata ata    688
Met Phe Arg Leu Leu Met Ala Ser Lys Lys Asp Asp Pro Gly Ile Ile
        110             115             120 atg aag tta aag gag cag cac tca aag gag ttg caa gca cat gtt gac    736
Met Lys Leu Lys Glu Gln His Ser Lys Glu Leu Gln Ala His Val Asp
        125             130             135 cag atc acc gag atg gca gca gta atg aga aaa gct att gaa att gac    784
Gln Ile Thr Glu Met Ala Ala Val Met Arg Lys Ala Ile Glu Ile Asp
140             145             150             155 gaa cag cag ggt tgc aag gaa cag cag cgc ata ttt caa ctt gaa caa    832
Glu Gln Gln Gly Cys Lys Glu Gln Gln Arg Ile Phe Gln Leu Glu Gln
                160             165             170 gaa aac aaa ggc ttg aga gag atc ctt cag ata act cga gaa tcc ttt    880
Glu Asn Lys Gly Leu Arg Glu Ile Leu Gln Ile Thr Arg Glu Ser Phe
                175             180             185 ttg aac ctt cag aag gat gat gcg tca gag agt aca tct ctg tcc gcc    928
Leu Asn Leu Gln Lys Asp Asp Ala Ser Glu Ser Thr Ser Leu Ser Ala
                190             195             200 tta gtg act aac agt gac ctg agt ctg agg aag agc tga gtggttggct    977
Leu Val Thr Asn Ser Asp Leu Ser Leu Arg Lys Ser
        205             210             215 gaggtcacta agacgggccc aggagtgagt ggatggatga acataaaccc aactccagtc   1037
agcctctttc ctctagtatg tcaggggcac tggcgaagag acagtagcag gatgtatagc   1097
cagtggtcat aaactagatc ccagtcacag ctcgacagga aaacctgggc cacagagtga   1157
acattgagtc tccaaggtgc tgctgaggac tgcaatttga gaagtgctgt tggcctcttg   1217
gatgagatat gggtcaccct gaatgctcct aataaacgtc ggaaagccta aattatcaca   1277
actccaaaag aaggttggtg tggtgttctg gatggaagac tttgttctga ttcctgtcct   1337
tctgttcagt gtcagagtca gcatagctta tgtatgtacc gcttctgtct cggtgctccc   1397 atcccctgc ccatctgttc atcgccggca gttcacattt acaggctata ggaatatgtc   1457
actcgcatca caaactgaag aaaggaatat acttgcacct agttcccata actcttaact   1517
agcaagttat tcgtgacttg cttgagtata tgtacctcag gaaggaagga aagacaagaa   1577
```

UNITED STATES PATENT AND TRADEMARK OFFICE
CERTIFICATE OF CORRECTION

PATENT NO. : 7,365,175 B2
APPLICATION NO. : 10/170786
DATED : April 29, 2008
INVENTOR(S) : Nishimura et al.

It is certified that error appears in the above-identified patent and that said Letters Patent is hereby corrected as shown below:

```
tatactttct aagaaagaca gttttatata gacacattta gtaggttaaa ctactttgag 1637 agactatgtt tggttctctg ttaacaatga gcctggctct tcctcctctc tacatgatgt 1697 ttaaggatac aggacagagg ggttggggat ttagctcagt ggtagagcgc ttgcctagca 1757 accgcaaggc cctgggttcg gtccccagct cctaaaaaaa gggaaaaaaa aaggataca  1817 ggatagctca ctagtacaca gagttggcat atttaatgta ataagatagg tatggtcatt 1877 tccaagtaaa tttggaattc tttggtattt aaaaaaacac ctcttcaaac atataagtaa 1937 gaaagcaggc tccaaaatca aagttctggg actgagtcta aaccctgttt agttcttata 1997 acctgtgatt tttccctaca acctgtgact canaaactgg cagtgaaagt gtgggcccac 2057 aggcattgtg ctttgcactt taaaaaaaaa aaagcttaag accacaagat agagaagtgt 2117 gctttaatac cattgcagcc taaactcttc tgtagtgatc agaataaaag aataaaagat 2177 tgtgaaatac ggcaaaaaat atacaatact tgtatgtgaa gttagcacag ataaaaagta 2237 aatcatttgt aagtacatat tactttgcag tgtaatttta tgtgtaattt catgtattgg 2297 caaaattcat aggacttta  cttgagaacc tttcattctg aagtttgagg tgagtggggt 2357 cataggtcag gtaggaaagg gccagtaccc caggtgataa accgttgtca tgcagaggcc 2417 ttaatatttt atatttaggt gaatttattt ctaagacttt tctattggtt ctgggagagt 2477 gtcccttagt ttagtggtca ttctttcatg tagtttggct ccaggccaga atcttagaag 2537 aaaggctaca cagttgagat gaggcagaat caaggagtga gtagttctat tgtgaaatgt 2597 tatttcagaa gtaattattt ttataaaaaa attatttact ctttgtcttc ttggatataa 2657 gtttaaggtt gtgaatattg aaagacattt gcattgttct tagcaagttt tccatccctc 2717 ctatcacccc cccctaaaa  aaaaaaaaa                                   2746
```

<210> 2
<211> 215
<212> PRT
<213> Rattus sp.

UNITED STATES PATENT AND TRADEMARK OFFICE
CERTIFICATE OF CORRECTION

PATENT NO. : 7,365,175 B2
APPLICATION NO. : 10/170786
DATED : April 29, 2008
INVENTOR(S) : Nishimura et al.

It is certified that error appears in the above-identified patent and that said Letters Patent is hereby corrected as shown below:

```
<400> 2
Met Ser Cys Thr Ile Glu Lys Ala Leu Ala Asp Ala Lys Ala Leu Val
 1               5                  10                  15
Glu Arg Leu Arg Asp His Asp Asp Ala Ala Glu Ser Leu Ile Glu Gln
                20                  25                  30
Thr Thr Ala Leu Ser Lys Arg Val Glu Ala Met Lys Gln Tyr Gln Glu
                35                  40                  45
Glu Ile Gln Glu Leu Asn Glu Val Ala Arg His Arg Pro Arg Ser Thr
            50                  55                  60
Leu Val Met Gly Ile Gln Gln Glu Asn Arg Gln Ile Arg Glu Phe Gln
 65                 70                  75                  80
Gln Glu Asn Lys Glu Leu Arg Thr Ser Leu Glu Glu His Gln Ser Ala
                85                  90                  95
Leu Glu Leu Ile Met Ser Lys Tyr Arg Glu Gln Met Phe Arg Leu Leu
                100                 105                 110
Met Ala Ser Lys Lys Asp Asp Pro Gly Ile Ile Met Lys Leu Lys Glu
                115                 120                 125
Gln His Ser Lys Glu Leu Gln Ala His Val Asp Gln Ile Thr Glu Met
            130                 135                 140
Ala Ala Val Met Arg Lys Ala Ile Glu Ile Asp Glu Gln Gln Gly Cys
145                 150                 155                 160
Lys Glu Gln Gln Arg Ile Phe Gln Leu Glu Gln Glu Asn Lys Gly Leu
                165                 170                 175
Arg Glu Ile Leu Gln Ile Thr Arg Glu Ser Phe Leu Asn Leu Gln Lys
                180                 185                 190
Asp Asp Ala Ser Glu Ser Thr Ser Leu Ser Ala Leu Val Thr Asn Ser
                195                 200                 205
Asp Leu Ser Leu Arg Lys Ser
                210                 215

<210> 3
<211> 762
<212> DNA
<213> Rattus sp.

<220>
<221> CDS
<222> (1)..(762)
<223> wound inducible transcript 3.0 beta (Wit 3.0 beta)

<400> 3
atg agc tgc acc att gag aag gca ctt gct gat gct aag gcc ctt gtt    48
Met Ser Cys Thr Ile Glu Lys Ala Leu Ala Asp Ala Lys Ala Leu Val
 1               5                  10                  15
```

UNITED STATES PATENT AND TRADEMARK OFFICE
CERTIFICATE OF CORRECTION

PATENT NO. : 7,365,175 B2
APPLICATION NO. : 10/170786
DATED : April 29, 2008
INVENTOR(S) : Nishimura et al.

It is certified that error appears in the above-identified patent and that said Letters Patent is hereby corrected as shown below:

```
gaa cgg ttg aga gac cat gat gat gca gca gag tct ctc atc gaa cag    96
Glu Arg Leu Arg Asp His Asp Asp Ala Ala Glu Ser Leu Ile Glu Gln
         20              25              30 acc act gcc ctc agc aag cga gtg gaa gcc atg aaa cag tat cag gaa   144
Thr Thr Ala Leu Ser Lys Arg Val Glu Ala Met Lys Gln Tyr Gln Glu
         35              40              45 gaa atc caa gaa ctt aat gaa gta gca aga cat cgg cca cga tcc aca   192
Glu Ile Gln Glu Leu Asn Glu Val Ala Arg His Arg Pro Arg Ser Thr
         50              55              60 cta gtt atg gga atc cag caa gaa aac aga caa atc aga gaa ttc caa   240
Leu Val Met Gly Ile Gln Gln Glu Asn Arg Gln Ile Arg Glu Phe Gln
65           70              75              80 caa gag aac aaa gaa ctg cgc aca tcc ttg gaa gag cac cag tct gcc   288
Gln Glu Asn Lys Glu Leu Arg Thr Ser Leu Glu Glu His Gln Ser Ala
             85              90              95 ttg gaa ctg ata atg agc aag tat cga gag cag atg ttc aga ttg cta   336
Leu Glu Leu Ile Met Ser Lys Tyr Arg Glu Gln Met Phe Arg Leu Leu
             100             105             110 atg gcc agc aag aag gac gac ccg ggc ata ata atg aag tta aag gag   384
Met Ala Ser Lys Lys Asp Asp Pro Gly Ile Ile Met Lys Leu Lys Glu
             115             120             125 cag cac tca aag att gac atg gta cat cgt aac agc tgc gaa gga ttc   432
Gln His Ser Lys Ile Asp Met Val His Arg Asn Ser Cys Glu Gly Phe
             130             135             140 ttc ctg gat gca tct cgg cac atc ctt gaa gca cct cag cac gga ctg   480
Phe Leu Asp Ala Ser Arg His Ile Leu Glu Ala Pro Gln His Gly Leu
145              150             155             160 gag agg agg cac ttg gaa gca aat cag aat gag ttg caa gca cat gtt   528
Glu Arg Arg His Leu Glu Ala Asn Gln Asn Glu Leu Gln Ala His Val
             165             170             175 gac cag atc acc gag atg gca gca gta atg aga aaa gct att gaa att   576
Asp Gln Ile Thr Glu Met Ala Ala Val Met Arg Lys Ala Ile Glu Ile
             180             185             190 gac gaa cag cag ggt tgc aag gaa cag cag cgc ata ttt caa ctt gaa   624
Asp Glu Gln Gln Gly Cys Lys Glu Gln Gln Arg Ile Phe Gln Leu Glu
             195             200             205
```

Page 6 of 8

UNITED STATES PATENT AND TRADEMARK OFFICE
CERTIFICATE OF CORRECTION

PATENT NO. : 7,365,175 B2
APPLICATION NO. : 10/170786
DATED : April 29, 2008
INVENTOR(S) : Nishimura et al.

It is certified that error appears in the above-identified patent and that said Letters Patent is hereby corrected as shown below:

```
caa gaa aac aaa ggc ttg aga gag atc ctt cag ata act cga gaa tcc    672
Gln Glu Asn Lys Gly Leu Arg Glu Ile Leu Gln Ile Thr Arg Glu Ser
    210                 215                 220 ttt ttg aac ctt cag aag gat gat gcg tca gag agt aca tct ctg tcc    720
Phe Leu Asn Leu Gln Lys Asp Asp Ala Ser Glu Ser Thr Ser Leu Ser
225                 230                 235                 240 gcc tta gtg act aac agt gac ctg agt ctg agg aag agc tga            762
Ala Leu Val Thr Asn Ser Asp Leu Ser Leu Arg Lys Ser
                245                 250

<210> 4
<211> 253
<212> PRT
<213> Rattus sp.

<400> 4
Met Ser Cys Thr Ile Glu Lys Ala Leu Ala Asp Ala Lys Ala Leu Val
 1               5                  10                  15
Glu Arg Leu Arg Asp His Asp Asp Ala Ala Glu Ser Leu Ile Glu Gln
                20                  25                  30
Thr Thr Ala Leu Ser Lys Arg Val Glu Ala Met Lys Gln Tyr Gln Glu
                35                  40                  45
Glu Ile Gln Glu Leu Asn Glu Val Ala Arg His Arg Pro Arg Ser Thr
            50                  55                  60
Leu Val Met Gly Ile Gln Gln Glu Asn Arg Gln Ile Arg Glu Phe Gln
65                  70                  75                  80
Gln Glu Asn Lys Glu Leu Arg Thr Ser Leu Glu Glu His Gln Ser Ala
                85                  90                  95
Leu Glu Leu Ile Met Ser Lys Tyr Arg Glu Gln Met Phe Arg Leu Leu
                100                 105                 110
Met Ala Ser Lys Lys Asp Asp Pro Gly Ile Ile Met Lys Leu Lys Glu
            115                 120                 125
Gln His Ser Lys Ile Asp Met Val His Arg Asn Ser Cys Glu Gly Phe
        130                 135                 140
Phe Leu Asp Ala Ser Arg His Ile Leu Glu Ala Pro Gln His Gly Leu
145                 150                 155                 160
Glu Arg Arg His Leu Glu Ala Asn Gln Asn Glu Leu Gln Ala His Val
                165                 170                 175
Asp Gln Ile Thr Glu Met Ala Ala Val Met Arg Lys Ala Ile Glu Ile
                180                 185                 190
Asp Glu Gln Gln Gly Cys Lys Glu Gln Gln Arg Ile Phe Gln Leu Glu
            195                 200                 205
Gln Glu Asn Lys Gly Leu Arg Glu Ile Leu Gln Ile Thr Arg Glu Ser
        210                 215                 220
```

Page 7 of 8

UNITED STATES PATENT AND TRADEMARK OFFICE
CERTIFICATE OF CORRECTION

| | |
|---|---|
| PATENT NO. | : 7,365,175 B2 |
| APPLICATION NO. | : 10/170786 |
| DATED | : April 29, 2008 |
| INVENTOR(S) | : Nishimura et al. |

It is certified that error appears in the above-identified patent and that said Letters Patent is hereby corrected as shown below:

```
Phe Leu Asn Leu Gln Lys Asp Asp Ala Ser Glu Ser Thr Ser Leu Ser
225                 230                 235                 240
Ala Leu Val Thr Asn Ser Asp Leu Ser Leu Arg Lys Ser
                245                 250
```

Signed and Sealed this

Fifteenth Day of December, 2009

David J. Kappos
*Director of the United States Patent and Trademark Office*